United States Patent [19]

Marsh

[11] 4,226,853

[45] Oct. 7, 1980

[54] FORMALINIZED ALLERGEN-CONTAINING SUBSTANCES AND PRODUCTION THEREOF

[76] Inventor: David G. Marsh, 11420 Harford Rd., Baltimore, Md. 21057

[21] Appl. No.: 550,535

[22] Filed: Feb. 18, 1975

Related U.S. Application Data

[63] Continuation-in-part of Ser. No. 289,284, Sep. 15, 1972, abandoned, which is a continuation of Ser. No. 865,481, Oct. 10, 1969, abandoned.

[30] Foreign Application Priority Data

Oct. 10, 1968 [GB] United Kingdom ............... 48064/68
Oct. 1, 1969 [GB] United Kingdom ............... 48189/69

[51] Int. Cl.³ .................... A61K 39/35; A61K 39/36; C07G 7/00
[52] U.S. Cl. ................................. 424/91; 260/112 R; 260/123.5; 424/85; 424/88; 424/95; 424/177
[58] Field of Search ....................... 424/88, 91, 85, 87, 424/177, 95; 260/112 R, 123.5

[56] References Cited

U.S. PATENT DOCUMENTS

| | | | |
|---|---|---|---|
| 2,019,803 | 11/1935 | Carter | 424/92 |
| 2,150,131 | 3/1939 | Rockwell | 424/92 |
| 3,135,662 | 6/1964 | Pope | 424/92 |

FOREIGN PATENT DOCUMENTS 1320769  2/1963  France.

OTHER PUBLICATIONS

Stull, The J. of Allergy, vol. 11, 1940, pp. 439–465.
Gold, Chem. Abs., vol. 36, 1942, p. 148.
Musiiko, Chem. Abs., vol. 57 19, pp. 10431i.
Gross, Chem. Abs., vol. 61, 1964, p. 2323.
Brit. J. Exptl. Path, vol. 44, 1963, p. 177.
Kabat, Exptl. Immunochem, C. C. Thomas, Springfield, 2nd. Ed., 1961 pp. 277–282, 459–461.
King, Biochemistry, vol. 1, Jul. 1962, pp. 709–720.

*Primary Examiner*—Anna P. Fagelson
*Attorney, Agent, or Firm*—Wills, Green & Mueth

[57] ABSTRACT

This invention relates to the production of formaldehyde treated allergens suitable for the immunotherapy (desensitization) of individuals suffering from allergies of the immediate type. These formalinized allergen-containing materials are also useful to induce formation of antibody in mammals which cross reacts with the native allergen-containing materials.

37 Claims, No Drawings

FORMALNIZED ALLERGEN-CONTAINING SUBSTANCES AND PRODUCTION THEREOF

CROSS-REFERENCE TO RELATED APPLICATIONS

This is a continuation-in-part of Ser. No. 289,284 filed Sept. 15, 1972, which was a continuation application of Ser. No. 865,481 filed Oct. 10, 1969, both now abandoned.

BACKGROUND OF THE INVENTION

Patients who suffer from allergies of the immediate type (atopies) have the capacity to make special kinds of allergic antibodies (reagins) upon exposure to certain substances (allergens) towards which they are sensitive. The reagins become strongly attached to certain tissues, particularly those of the epithelium. Following a subsequent exposure to the sensitizing allergenic material, a physical combination occurs between the allergen(s) and their homologous reagins, resulting in allergic manifestations at the sites of reagin-allergen combination. Allergic individuals are also able to produce the so-called "blocking antibodies" of a non-reagin type which are capable of combining with and inactivating the allergen, generally without any undesirable side reactions. Reaginic activity has been attributed to Immunoglobulin E (IgE) and "blocking" activity mainly to IgG in the serum and IgA in secretions.

The term "allergic" as used here will be restricted to defining allergies of the immediate (atopic) type.

It has long been the clinical practice to inject an allergic patient with gradually increasing doses of aqueous extracts containing the allergenic material(s) toward which the patient is sensitive. The rationale behind this treatment is primarily to build up the concentration of protective blocking antibody in the serum (and other body fluids) to a level where it can effectively compete with the tissue-fixed reagin for allergen which enters the body, thereby inhibiting the allergic reactions. In certain cases, this therapy has also been found to suppress the production of reagins and to decrease the cellular responsiveness toward the injected allergens. The immunizing doses of the allergenic extract must be increased very gradually during the course of the treatment in order to minimize the risk of a general allergic (anaphylactic) response in the patient.

The main disadvantages of this immunotherapy are: (i) repeated injections are required over many weeks, (ii) the treatment is seldom completely effective in alleviating the allergic syndrome and (iii) the risk of general anaphylactic reaction is always present at each stage of the treatment.

The original therapy has, therefore, been modified with the aim of overcoming these disadvantages. More recent forms of treatment include immunizing the patient with either a water-in-oil emulsion of the allergenic extract or by including a slow release adjuvant such as an alginate with an extract of the allergenic material. Such methods have not proved to be entirely satisfactory due to the occurrence of some anaphylactic and some toxic reactions in the patient or to the failure of these preparations to be completely effective clinically.

Several workers have treated allergenic materials chemically or physically in an attempt to reduce substantially their allergenic properties, but retain their capacity to protect an allergic individual against the native allergen. Immunotherapy of allergic individuals using such modified allergens would, it was hoped, retain the desired immunizing properties of the native allergen, primarily in the sense that blocking antibody against the native allergen would be produced in significant quantity. Furthermore, the reduced allergenicity of such modified materials would permit the use of greatly increased doses of immunizing material and, thus, greatly enhance the quantity of protective blocking antibody produced.

It has now been found that, by a new process employing formaldehyde solution, the great majority of allergen-containing substances may be so modified that the said disadvantages of the native allergens with regard to their use in immunotherapy are overcome. Hereinafter, any allergen-containing substance will be referred to simply as an allergen, although it is recognized that not all components of an allergen-containing substance are necessarily allergenic. In referring to the new formaldehyde treatment the terms "formalinized" and "formalinization" will be restricted to describing the treatment of amino-containing allergenic materials with formaldehyde where definite chemical reaction takes place between amino groups and formaldehyde, involving the establishment of inter- or intramolecular methylene bridge linkages between or within the allergen molecules themselves or between allergen and other reactive molecules present in the reaction mixture.

SUMMARY OF THE INVENTION

The novel formalinized allergens of this invention are produced by allowing allergens, dissolved in a non-phenolic aqueous solution, to react chemically under mild conditions with dilute formaldehyde or a formaldehyde-liberating substance such as methenamine also present in the solution. The allergens so treated may be highly purified or crude extracts. As used herein, the term "non-phenolic" is intended to mean that at most only trace amounts of added phenolic compounds are present in the environment of the formalinization reaction. However, this term does not preclude the presence of phenolic hydroxy groups in the allergens per se which are known to naturally contain, in some instances, such groups as part of the complex proteinaceous structure.

I have found that the procedure of this invention leads to formalinized allergens with desired immunizing properties, such formalinized allergens being suitable for the immunotherapy of allergic humans. These derivatives are also useful for the immunization of other mammals to produce antibody strongly cross-reactive with the native allergen.

While not bound by any theory, I believe that one major reason why my formalinized allergens are superior to previously prepared formaldehyde-treated allergens lies in the absence of phenol from my reaction solution. Phenol present in reaction solutions of earlier workers would have preferentially been incorporated into resultant products due to chemical reaction between aminomethylol groupings on the amino-containing allergens (intermediates of type A in the equation below) and phenol. Such chemical substitution of phenolic groupings into amino-containing molecules is known to lead to derivatives whose predominant immunizing properties reflect to a very significant degree the phenolic determinants rather than other regions of the molecule. Thus, formaldehyde-treated allergens incorporating phenol would not possess desired immunizing properties as heretofore defined, since immunotherapy with such materials would lead to antibody directed principally against the newly incorporated phenolic groups rather than against original parts of the allergen against which antibody must be produced in significant amount if desired immunizing properties are to result.

In contrast with previous work, immunization with the formalinized allergens of this invention leads to the extensive production of antibody against some native parts of the allergen molecules; a large proportion of this antibody is capable of exerting a blocking affect on the native allergen molecules.

Where crude allergens are used, fatty substances and low molecular weight non-allergenic materials in the native substances should preferably although not necessarily have been removed prior to formalinization. The reaction between the crude or highly purified allergenic materials and the formaldehyde may be carried out in the presence of a low molecular weight additive. Suitable additives, usually containing less than about eight carbon atoms in addition to any functional groups present, include: aliphatic diamines; guanidines; aliphatic acid amides; aliphatic carboxylic acids containing amino groups, including aliphatic amino acids (monoamino monocarboxylic acids, monoamino dicarboxylic acids and diamino monoccarboxylic acids) aliphatic hydroxyamino acids, and aliphatic diamino dicarboxylic acids; and aliphatic compounds containing combinations of permutations of one or more amino, guanidino and acid amido groups. In addition, a limited number of hydroxy groups may be present in any of the above types of compounds. Species include 1,4-diaminobutane, lysine, orithinine, 1,5-diamino-pimelic acid, arginine, adipamide, aspartic acid, serine and alanine. The additive is such that it chemically combines with the pollen components during the formalinization process. As compared with formalinized allergens prepared by treatment with formaldehyde alone, some of the formalinized allergens prepared in combination with an additive process to a greater degree the desired immunizing properties discussed earlier.

DESCRIPTION OF PREFERRED EMBODIMENTS

While not bound by any theory, under the reaction conditions used in this invention, it is believed that the formaldehyde reacts reversibly with free amino groups on proteins, peptides and amino acids and also with the amino groups of amino sugars present in the reaction mixture. Using, R, R$^I$, etc. to represent protein, peptide, amino acid, glycoprotein and other possible residues which might be chemically linked to the reactive groupings shown below, the following series of reactions are believed to occur:

$$R-NH_2 + CH_2O \rightleftharpoons R-NHCH_2OH \tag{A}$$

The unstable aminomethylol group, intermediate (A), which may be present on the allergen molecules themselves or on additives or other non-allergenic substances occurring with the allergen, may then react with certain other reactive groups to form the more stable methylene bridge structures in the following manner:

(a) With guanidino groups of arginine (on proteins, peptides or any additive containing guanidino group(s)—e.g., arginine):

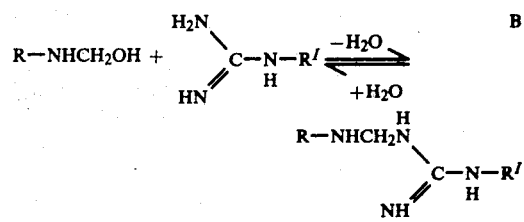

(b) With acid amides (on proteins, peptides, additives containing acid amide grouping(s)—e.g., adipamide):

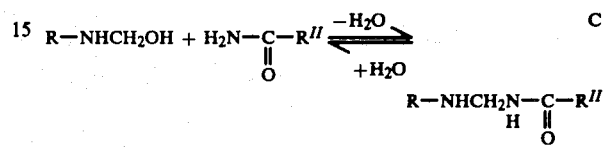

(c) With certain aromatic groups (on proteins, etc.—e.g., tyrosyl residues in proteins):

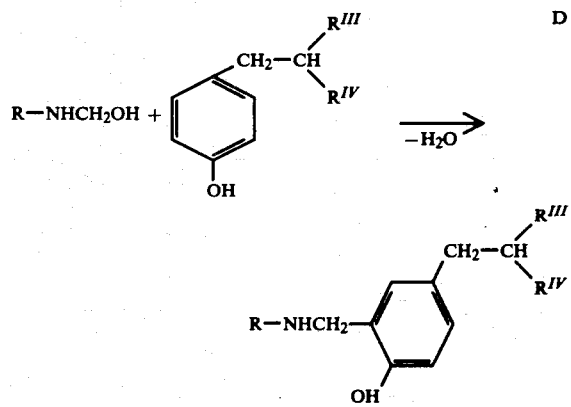

The stability of the derivatives is generally in the order: D>C>B.

Hence, any allergenic determinant containing an amino group, a guanidino group, an acid amide or a reactive aromatic residue (e.g., tyrosine, tryptophan or histidine) may be modified and, potentially, may be rendered non-allergenic by formaldehyde treatment. Furthermore, an allergenic determinant not comprised of the above groupings may be modified and rendered non-allergenic by reactions occurring at adjacent (or even, at relatively remote regions) on the allergen molecule, providing there is an ensuing steric alteration in the allergenic determinant such that it is no longer recognized as such by the homologous reagin.

It should further be noted that when a relatively large excess of an additive is present, it will preferentially take part in those reactions involving its reactive groupings and formaldehyde, rather than the occurrence of similar reactions involving analogous reactive groupings on the allergen molecule with formaldehyde. For example, when a lysine additive is present, the net result would be for most of the available guanidino, acid amide and the reactive aromatic residues of an allergen molecule to be linked through methylene bridges to the lysine additive rather than to lysine residues on the allergen molecule itself.

Closely-related plant and animal species produce many materials which are often similar both antigenically and allergenically. For example, nearly all grass pollens (especially those which are of primary importance in hay fever) contain three important but distinct groups of immunochemically closely related allergens, which have been classified as Groups I, II and III, and of which Group I is of major importance allergenically. Hence, a Group I allergen of one grass pollen may be used to prepare a formalinized derivative which possesses desired immunizing properties in respect to native Group I of many species of grass pollen. A desired immunizing grass pollen formalinized allergen preparation may, therefore, be prepared from an extract of a mixture of a relatively small number of different grass pollens (e.g., from perhaps 4 to 6 different species, selected to contain a representative cross-section of the various immunochemical grass pollen allergenic groups which are causative agents in hay fever).

Crude allergenic preparations which are particularly suitable for formalinization may be prepared by defatting the native allergen-containing materials with anhydrous peroxide-free ether and extracting the defatted materials with an aqueous solution buffered to about pH 6-8 (e.g., 0.125 M $NH_4HCO_3$). Low molecular weight non-allergenic substances, if present, may then be removed from the extract by dialysis through a semipermeable membrane (e.g. Visking tubing), although gel filtration, or a similar process familiar to those skilled in the art, may be used to achieve a similar result; alternatively, the high molecular weight materials may be precipitated without significant irreversible denaturation from the whole extract by a salt or solvent precipitation process, and these high molecular weight materials may be reconstituted from the precipitated materials in the form of an aqueous solution. Purified, or partially purified, allergenic substances may be prepared by any of the procedures commonly used for purification of macromolecules from complex mixtures. Suitable purification processes have been described in the literature for fish allergens, ragweed pollen and rye grass pollen, although these are not the only procedures nor the only allergenic materials which may be used in the formalinization process.

The present invention is not restricted to any particular allergen-containing material or extract. However, plant pollen allergen-containing materials, particularly those of grasses, trees and weeds important in allergy, may be extracted and treated successfully with formaldehyde in accordance with this invention. Examples of pollens from the grass family (*Gramineae*) which are useful in the practice of this invention include meadow fescue (*Festuca elatior*), smooth-stalked meadow (*Poa pratensis*) and cocksfoot (*Dactylis glomerata*) of the tribe Festuceae, common rye grass (*Lolium perenne*) and Italian rye grass (*Lolium multiflorum*) of the tribe *Hordeae*, timothy (*Phelum pratense*) and fine bent (*Agrostis palustris*) of the tribe *Agrostideae* and sweet vernal (*Anthoxanthum odoratum*) of the tribe *Phalarideae*. Comparable examples of tree pollens include various species of walnut, such as *Juglans californica*, of birch (e.g. *Betula alba*) of oak (e.g. *Quercus alba*) and of elm (e.g. *Ulmus parvifolia*). Useful weed pollens include short ragweed (*Ambrosia elatior*), tall ragweed (*Ambrosia trifida*), Russian thistle (*Salsola pestifer*), common sage (*Artemisia tridentata*) and English plantain (*Plantago lanceolata*). Other allergenic materials which can be treated include: extracts containing whole bodies and/or excreta and secreta of house dust mites of the genus *Dermatophagoides* and related genera, such extracts to include crude extracts of house dust; solutions of food allergens such as ovalbumin, extracted from hens' eggs; extracts of moulds (e.g. *Alternaria, Penicillium, Aspergillus, Helminthosporium,* etc.); extracts of plant seeds and fibers (e.g. cotton, castor, etc.); and extracts of stinging insects (e.g. bees and wasps).

Highly purified or partially purified allergens may also be formalinized, for example, Group I grass pollen allergens, Antigen E of ragweed pollen and partially purified house dust mite extracts.

The concentrations of allergen, formaldehyde and any additive present in the reaction mixture and the temperature, pH and period of incubation of the reaction mixture which result in optimal conditions of formalinization are interdependent to some degree. The following conditions are preferred, each condition being subject to maintaining other conditions within appropriate limits in order to achieve a desired formalinized allergen. In any reaction solution a preservative such as sodium o-(ethyl-mercurithio) benzoate ('Merthiolate') may be added to the reaction solution (1:10,000).

The final concentration of the allergenic materials used for the formaldehyde reaction should preferably (i) be such that all components are completely soluble, and (ii) be compatible with the concentration of formaldehyde and any additive used. The solutions should be prepared in an aqueous buffer preferably of about pH 7.5 of a suitable molarity to maintain this pH to about ±1.0 during the course of the reaction in order to optimize the occurrence of the desired formaldehyde reactions. Concentrations of up to about 4 mg. of allergenic materials per ml of 0.1 M sodium phosphate buffer at pH 7.5 usually meet the aforementioned requirements.

The concentration of formaldehyde in the reaction mixture (formaldehyde exists in aqueous solution partly as hydrated polymers and hydrates of formaldehyde) should not be so great as to affect adversely the desired immunizing properties of the resultant formalinized allergen, but should be sufficient to result in virtually complete destruction of the allergenicity of the native allergen. In addition to the aforestated factors, preferred formaldehyde concentration ranges vary according to the stability and purity of the allergen being treated.

For relatively stable crude allergens from which low molecular weight non-allergenic materials have been removed (e.g. dialysed grass pollen extracts), formaldehyde concentrations of between 0.24 M and 0.50 M, but preferably about 0.36 M, have been used successfully with dialysed pollen solid concentrations of 2 mg/ml and where no additives were present. In such cases, much lower formaldehyde concentrations (e.g. 0.06 M) were found to lead to rather allergenic derivatives while much higher formaldehyde concentrations (e.g. above 5 M) would have led to extensive denaturation, partial or complete precipitation of the allergens and loss of desired immunizing properties.

Where native crude extracts which still contain substantial amounts of low molecular weight materials are to be utilized (e.g. native grass pollen extracts which contain up to about 85 percent by weight of non-allergenic compounds of molecular weight under about 4000), concentrations of formaldehyde appreciably higher than 0.36 M should be used where the extracts contain the equivalent of about 2 mg/ml of non-dialysable solids. In such cases, the low molecular weight substances essentially represent undesirable "additives"

in the solutions; hence, I do not prepare formalinized allergens from such native crude extracts by preference.

With highly purified, relatively stable allergens such as Group I grass pollen allergens, formaldehyde concentrations of between about 0.025 M and 0.12 M are preferred with allergen concentrations of about 1 mg/ml.

For highly unstable allergens, particularly ragweed's Antigen E, the above ranges do not necessarily apply. In such cases, lower incubation temperatures and short incubation periods are preferred and the formaldehyde concentration should be adjusted to optimize loss of allergenicity and retention of the desired immunizing properties.

A low molecular weight additive, where present, should preferably be an aliphatic amine or diamine without additional functional groups capable of reacting with either formaldehyde or an aminomethylol group (intermediate A discussed above). Alternatively, the additive may be an aliphatic compound containing carboxylic acid amide group(s) or both amino and carboxylic acid amide groups. Guanidino compounds such as arginine may also be used. Examples of additives which are particularly efficacious in conferring the desired properties on the resultant formalinized allergens are $\alpha, \omega$-aliphatic diamines and certain derivatives thereof, preferably with a linear paraffin carbon chain length of $C_4$ or $C_5$ (e.g. lysine), or dicarboxylic acids such as adipamide. Mixtures of additives may also be used. The total concentration of the additive should be compatible with the concentration of formaldehyde used; a preferred working range of additive is about 0.02 M to 0.2 M, more preferably 0.05 M with purified allergens (1 mg/ml) treated with 0.06 M formaldehyde and 0.1 M with dialyzed crude allergenic extracts (2 mg/ml).

For allergens which are relatively stable in solution, a preferred incubation temperature is 32° C. ($\pm 2°$ C.), although temperatures up to about 40° C. may be used. Too high a temperature may result in the formation of undesirable formalinized products. For example, substantial crosslinking and denaturation may result at high temperatures. For relatively stable allergens, such as the Group I grass pollen allergens, the incubation time generally is about 4 weeks. Such allergens incubated at 32° C. ($\pm 2°$ C.) for shorter incubation periods of about 2 weeks or less are more allergenic than those treated for 4 weeks under the same conditions. Longer incubation periods at temperatures of 32° C. or lower may be utilized, limited primarily by considerations of economy and efficiency.

Particularly with regard to heat labile allergens, such as ragweed antigen E, temperatures of the order of 5° C. to 15° C. are to be preferred, although lower temperatures down to the freezing point of the incubation mixture may be employed. With temperatures under 5° C., however, an extensive incubation period may be necessary. The actual incubation period to be used under given conditions of temperature, formaldehyde concentration and allergen concentration is carefully selected in order to optimize loss of allergenic reactivity and retention of desired immunizing properties.

The low molecular weight additive may be added at any stage during the incubation, provided there is sufficient time for reaction between the allergen and the additive. If the mixture is still appreciably allergenic at the termination of the incubation period, additional amounts of formaldehyde solution with or without additive may be added and the incubation period extended until a stable, non-allergenic mixture is produced with the desired immunizing properties.

The aqueous formalinized allergen preparations so obtained contain immunizing substances which may be rendered free from unreacted formaldehyde and additive by dialysis, gel filtration, or by precipitating the allergen-containing material from solution by means of a suitable salt or solvent precipitant. In certain cases, the concentrations of free formaldehyde may be so low as to render such an operation unnecessary. The formalinized allergen preparations may be stored in solution at about 4° C. under sterile conditions or frozen; alternatively they may be freeze-dried and stored dry in cases where the normal process of freeze-drying does not affect the desired immunizing properties of the formalinized allergen preparation.

The formalinized allergen, prepared as described above, is suitable immunotherapeutic agents for mammals, including allergic humans. An adjuvant such as an alum or an alginate can be incorporated into the desired immunizing preparation to enhance the immunogenic efficiency. The formalinized allergen can also be used in diagnostic testing both before and during immunotherapy of allergic humans.

The formalinized allergens of my invention can be administered to mammals in conventional manner such as intradermally, subcutaneously or intramuscularly. In addition, the low allergenicity of these materials permits administration in the form of an aerosol spray to the nose and/or mouth to achieve immunization transmucosally.

This invention is illustrated, but not limited, by the following examples:

EXAMPLE I

A freeze-dried Group I allergen preparation from the pollen of common rye grass (*Lolium perenne*) was prepared to a high degree of purity as described by Johnson & Marsh (European Polymer J., 1, 63 [1965]).

In Method 1a, a stock solution of this Group I allergen was prepared by dissolving the dry allergen (100 mg) in 0.1 M $Na_2HPO_4$ (72.0 ml), containing 1 part 'Merthiolate' per 10,000 parts of solution. To an aliquot of this solution (21.6 ml), 36% w/v formaldehyde solution (50 $\mu$l) was added very slowly with constant magnetic stirring of the mixture. The pH of the mixture was adjusted to pH 7.50$\pm$0.10 by addition of 0.5 N NaOH and finally brought to a total volume of 24.0 ml by addition of a Solution A (a 0.1 M $Na_2HPO_4$—$NaH_2PO_4$ buffer solution at pH 7.50, containing 1 part 'Merthiolate' per 10,000 parts of buffer).

In Method 1b, the dry allergen (100 mg) was dissolved in Solution A (50 ml) to give a second stock solution of the allergen. To an aliquot of this solution (12.0 ml), Solution A (6.0 ml) was added, followed by 0.3 M formaldehyde solution (4.8 ml) prepared in Solution A, keeping the mixture well stirred. The pH of the mixture was adjusted to pH 7.50 and the total volume to 24.0 ml as described in Method 1a.

The final mixtures in Methods 1a and 1b contained 0.025 M and 0.06 M formaldehyde and allergen concentrations of 1.25 and 1.0 mg/ml, respectively. In both cases, the mixtures were sterilized by membrane filtration prior to incubation at 32° C.$\pm 1°$ C. for 28–32 days. At the termination of the incubation period, the mixtures were dialysed against Solution A to remove unreacted formaldehyde and stored frozen; alternatively, they were dialysed against 0.002 M $NH_4HCO_3$, freeze-dried and stored at $-20°$ C. These preparations will be referred to as "normal formalinized allergen" of rye Group I allergen.

EXAMPLE II

All procedures were as described in either Method 1a or Method 1b, except that in Method 2a, L-lysine monohydrochloride (219 mg) was dissolved in a second aliquot (21.6 ml) of the allergen stock solution of Method 1a prior to adding the formaldehyde; in Method 2b, a solution of 0.2 M L-lysine monohydrochloride (6.0 ml), prepared in 0.1 M $Na_2HPO_4$ containing 'Merthiolate' (1:10,000), was added to a second aliquot (12.0 ml) of the allergen stock solution of Method 1b, replacing the Solution A (6.0 ml) used at this stage in Method 1b. In both methods, the incubation mixtures contained 0.05 M lysine as the additive. These preparations will be referred to as "lysine formalinized allergen" of rye Group I allergen.

EXAMPLE III

All procedures were as described in Method 2b except that, to a third aliquot (12.0 ml) of the allergen stock solution of Method 1b, 0.2 M L-arginine monohydrochloride (6.0 ml) in 0.1 M $Na_2HPO_4$ containing 'Merthiolate' (1:10,000), was substituted for the equivalent amount of L-lysine monohydrochloride used in Method 2b. This preparation will be termed "arginine formalinized allergen" of rye Group I allergen.

EXAMPLE IV

All procedures were as described in Example I, Method 1b, except that the freshly-prepared sterile solution (24.0 ml) at pH 7.50, containing the Group I rye allergen (1.0 mg/ml) and 0.06 M formaldehyde, was injected into a presterilized bottle containing sterile adipamide (172.8 mg, giving the equivalent of a 0.05 M solution). The bottle was gently shaken in order to dissolve as much of the adipamide as possible prior to incubation at 32° C. The adipamide, partially insoluble initially, gradually dissolved during the period of incubation. The resultant preparation will be described as an "adipamide formalinized allergen" of rye Group I allergen.

EXAMPLE V

A mixture of equal weights of the dried pollens of five grasses, Italian rye (*Lolium multiflorum*), meadow fescue *(Festuca elatior)*, cocksfoot (*Dactylis glomerata*), timothy (*Phleum pratense*) and smooth-stalked meadow (*Poa pratensis*), was defatted by extraction with dry peroxide-free ether. The pollen mixture was then extracted with ten times its original total weight of 0.125 M $NH_4HCO_3$ (pH 7.8) for 24 hours at 4° C. (final pH of extract, 7.7). The extract was centrifuged and extensively dialysed in a Visking 18/32 in. dia. dialysis tubing against six changes of 0.002 M $NH_4HCO_3$ and finally against distilled water. The solution in the dialysis sac was clarified by centrifugation and freeze-dried.

A solution of the dry dialysed pollen material at a concentration of 4 mg/ml was prepared in Solution A (see Example I) and centrifuged to remove a trace of insoluble material. The procedure for formaldehyde treatment of an aliquot of this solution (12.0 ml) followed the same pattern as that described in Method 1b (Example I). In this case, the total concentration of pollen solids in the incubation mixture was 2.0 mg/ml; the formaldehyde concentration was 0.36 M as in Method 1b. This preparation will be described as a "normal formalinized allergen" of dialysed mixed grass pollen extract.

EXAMPLE VI

A mixture of dialysed grass pollen materials containing by weight 3 parts cocksfoot (*Dactylis glomerata*), 3 parts timothy (*Phleum pratense*), 2 parts sweet vernal (*Anthoxanthum odoratum*), 1 part smooth-stalked meadow (*Poa pratensis*) and 1 part fine bent (*Agrostis palustris*) was used in place of the dialysed mixed grass extract of Example V. In other respects, all conditions of reaction and reactant concentrations were the same as described in Example V.

EXAMPLE VII

A lysine formalinized allergen preparation was prepared from the solution of dialysed mixed grass pollen material described in Example VI by incubation in the presence of 0.36 M formaldehyde and 0.1 M L-lysine, using a procedure analogous to that described in Example II, Method 2b. The concentration of pollen material in the incubation mixture was 2 mg/ml as in Example VI.

EXAMPLE VIII

A dialysed extract of the pollen of California black walnut (*Juglans californica*) was prepared and reacted with formaldehyde in a manner analogous to the dialysed grass pollen extract of Example V.

EXAMPLE IX

A dialysed extract of the pollen of Chinese evergreen elm (*Ulmus parvifolia*) was prepared and reacted with formaldehyde in a manner analogous to the dialysed grass pollen extract of Example V.

EXAMPLE X

An extract of a crude preparation of the house-dust mite (*Dermatophagoides pteronyssinus*) grown on human skin scales and yeast extract was prepared and dialysed in a manner similar to that described for the grass pollen extract of Example V. Except for the substitution of dialysed mite extract (2 mg/ml) for the dialysed grass pollen extract of Example V, all reaction conditions and reactant concentrations were the same as in Example V.

EXAMPLE XI

The rye Group I of Methods 1b and 2b, described above, was replaced with ovalbumin (3 times crystallized, from hens' eggs). The reaction with formaldehyde was conducted as previously described.

The allergenic and antigenic properties of formalinized allergens were examined and compared with the respective properties of the native allergens from which they were derived.

Allergenic properties were investigated qualitatively by scratch skin tests in large numbers of allergic humans, semi-quantitatively by intradermal skin testing and direct broncho-provocative assay in several allergic humans and quantitatively by measuring the histamine released from human leucocyte suspensions (isolated from about 15 different allergic individuals), following challenge with formalinized or native allergens.

Two aspects of cross-antigenicity between formalinized and native allergens were investigated; namely, (i) cross-reactogenic properties: the ability of a formalinized allergen to combine with antisera produced (in rabbits) against the native allergen, and (ii) cross-immunogenic properties: the ability of formalinized allergen to induce the formation (in guinea pigs) of antibody which would block native allergen-induced allergic histamine release from isolated allergic human leucocytes and which would cross-react with the native allergen in tests such as passive cutaneous anaphylaxis (PCA) in normal guinea pigs. With respect to determining quantitatively the existence of desired immunizing properties in a formalinized allergen, the blocking of allergen-mediated allergic histamine release from human leucocytes was a critical test.

RESULTS

The formalinized allergens of this invention were found to have lost substantially the allergenic properties, but to have retained to a high degree the antigenic properties, (including desired immunizing properties), of the native allergen. Loss of allergenicity varied according to the individual tested, the presence or absence of additives in the formalinized allergen and the type of allergenicity test employed, with ranges being about 200–1,000,000 times less allergenicity (commonly, 1,000–10,000 times less) in the formalinized allergen than in the native allergen. The cross-antigenicity between the formalinized allergen and the native allergen was commonly 20–100%. In many cases, the desired immunizing properties of the formalinized relative to the native allergen had been retained by 60–100%.

Thus, formalinized allergens of this invention were found to be greatly superior to the native allergens for use in allergic human immunotherapy, since the ratio of desired immunizing properties compared to allergenicity had been increased very substantially.

Having fully described the invention, it is intended that it be limited only by the scope of the amended claims.

I claim:

1. A process for producing a formalinized allergen of low allergenic activity in allergic humans and which is capable of inducing in mammals the formation of blocking antibody against the native allergen in significant concentration, comprising: (1) extracting an allergen-containing material with an aqueous solution; (2) removing essentially all of the low molecular weight non-allergenic substances from the soluble part of the said extract to leave the allergen-containing materials in said solution; (3) adding formaldehyde to the said solution of allergen-containing materials to give a concentration of formaldehyde from about 0.06 M to 5.0 M; (4) treating the aqueous extract of material containing said allergens with said formaldehyde solution in a non-phenolic environment at a temperature from about the freezing point of the incubation mixture up to about 40° C.; and (5) incubating the same at a temperature below that which the allergen undergoes substantial heat denaturation and generally from about the freezing point of the incubation mixture up to about 40° C. until the substantial formation of inter- or intramolecular methylene bridge linkages occurs in said solution and the allergenic determinant groups are modified to result in substantial reduction of allergenic properties while largely retaining the desired immunizing properties.

2. The process of claim 1 wherein the incubation is subsequently extended with the addition of more formaldehyde.

3. A process of claim 1 wherein there is present along with said dilute formaldehyde solution at least one additive selected from the group consisting of 1,4-diaminobutane, lysine, ornithine, 1,5-diamino-pimelic acid, arginine, adipamide, aspartic acid, serine and alanine.

4. The process of claim 1 wherein the allergen-containing material is an aqueous extract of a grass pollen substance.

5. The process of claim 1 wherein the allergen-containing material contains a Group I grass pollen allergen preparation.

6. The process of claim 1 wherein the allergen-containing material is an aqueous extract of a weed pollen substance.

7. The process of claim 1 wherein the allergen-containing material contains ragweed pollen's Antigen E.

8. The process of claim 1 wherein the allergen-containing material is an aqueous extract of a tree pollen substance.

9. The process of claim 1 wherein the allergen-containing material is an aqueous extract containing house dust mites or their residues.

10. The process of claim 1 wherein the allergen-containing material is a purified allergen preparation.

11. A process for producing a formalinized allergen of low allergenic activity in allergic humans and which is capable of inducing in mammals the formation of blocking antibody against the native allergen in significant concentration, comprising: (1) extracting an allergen-containing material with an aqueous solution; (2) removing essentially all of the low molecular weight non-allergenic substances from the soluble part of the said extract to leave the allergen-containing materials in said solution; (3) adding formaldehyde to the said solution of allergen-containing materials to give a concentration of formaldehyde from about 0.06 M to 4.0 M; (4) treating the aqueous extract of material containing said native allergen with said formaldehyde solution in a non-phenolic environment at a temperature from about 15° C. to about 32° C.; and (5) incubating the same at a temperature below that which the allergen undergoes substantial heat denaturation and generally from about 15° C. to about 32° C. until the substantial formation of inter- or intramolecular methylene bridge linkages occurs in said solution and the allergenic determinant groups are modified to result in substantial reduction of allergenic properties while largely retaining the desired immunizing properties.

12. The process of claim 11 wherein there is present along with said dilute formaldehyde solution at least one additive selected from the group consisting of 1,4-diaminobutane, lysine, ornithine, 1,5-diamino-pimelic acid, arginine, adipamide, aspartic acid, serine and alanine.

13. The process of claim 11 wherein the allergen-containing material is an aqueous extract of a grass pollen substance.

14. The process of claim 11 wherein the allergen-containing material contains a Group I grass pollen allergen preparation.

15. The process of claim 11 wherein the allergen-containing material is an aqueous extract of a weed pollen substance.

16. The process of claim 11 wherein the allergen-containing material contains ragweed pollen's Antigen E.

17. The process of claim 11 wherein the allergen-containing material is an aqueous extract of a tree pollen substance.

18. The process of claim 11 wherein the allergen-containing material is an aqueous extract containing house dust mites or their residues.

19. The process of claim 11 wherein the allergen-containing material is a purified allergen preparation.

20. A formalinized allergen of low allergenic activity in allergic humans and which is capable of inducing in mammals the formation of blocking antibody against the native allergen in significant concentration, prepared by: (1) extracting an allergen-containing material with an aqueous solution; (2) removing essentially all of the low molecular weight non-allergenic substances from the soluble part of the said extract to leave the allergen-containing materials in said solution; (3) adding formaldehyde solution to the said solution of allergen-containing materials to give a concentration of formaldehyde from about 0.06 M to 5.0 M; (4) treating the aqueous extract of material containing said allergens with said formaldehyde solution in a non-phenolic environment at a temperature from about the freezing point of the incubation mixture up to about 40° C.; and (5) incubating the same at a temperature below that which the allergen undergoes substantial heat denaturation and generally from about the freezing point of the incubation mixture up to about 40° C. until substantial formation of inter- or intramolecular methylene bridge linkages occur in said solution and the allegenic determinant groups are modified to result in substantial reduction of allergenic properties while largely retaining the desired immunizing properties.

21. The product of claim 20 wherein there is present along with said dilute formaldehyde solution at least one additive selected from the group consisting of 1,4-diamino-butane, lysine, ornithine, 1,5-diamino-pimelic acid, arginine, adipamide, aspartic acid, serine and alanine.

22. The product of claim 20 wherein the allergen-containing material is an aqueous extract of a grass pollen substance.

23. The product of claim 20 wherein the allergen-containing material contains a Group I grass pollen allergen preparation.

24. The product of claim 20 wherein the allergen-containing material is an aqueous extract of a weed pollen substance.

25. The product of claim 20 wherein the allergen-containing material contains ragweed pollen's Antigen E.

26. The product of claim 20 wherein the allergen-containing material is an aqueous extract of a tree pollen substance.

27. The product of claim 20 wherein the allergen-containing material is an aqueous extract containing house dust mites or their residues.

28. The product of claim 20 wherein the allergen-containing material is a purified allergen preparation.

29. A formalinized allergen of low allergenic activity in allergic humans and which is capable of inducing in mammals the formation of blocking antibody against the native allergen in significant concentration, prepared by: (1) extracting an allergen-containing material with an aqueous solution; (2) removing essentially all of the low molecular weight non-allergenic substances from the soluble part of the said extract to leave the allergen-containing materials in said solution; (3) adding formaldehyde solution to the said solution of allergen-containing materials to give a concentration of formaldehyde from about 0.06 M to 4.0 M (4) treating the aqueous extract of material containing said allergens with said formaldehyde solution in a non-phenolic environment at a temperature from about 15° C. to about 32° C.; and (5) incubating the same at a temperature below that which the allergen undergoes substantial heat denaturation and generally from about 15° C. to about 32° C. until substantial formation of inter- or intramolecular methylene bridge linkages occur in said solution and the allergenic determinant groups are modified to result in substantial reduction of allergenic properties while largely retaining the desired immunizing properties.

30. The product of claim 29 wherein there is present along with said dilute formaldehyde solution at least one additive selected from the group consisting of 1,4-diaminobutane, lysine, ornithine, 1,5-diamino-pimelic acid, arginine, adipamide, aspartic acid, serine and alanine.

31. The product of claim 29 wherein the allergen-containing material is an aqueous extract of a grass pollen substance.

32. The product of claim 29 wherein the allergen-containing material contains a Group I grass pollen allergen preparation.

33. The product of claim 29 wherein the allergen-containing material is an aqueous extract of a weed pollen substance.

34. The product of claim 29 wherein the allergen-containing material contains ragweed pollen's Antigen E.

35. The product of claim 29 wherein the allergen-containing material is a aqueous extract of a tree pollen substance.

36. The product of claim 29 wherein the allergen-containing material is an aqueous extract containing house dust mites or their residues.

37. The product of claim 29 wherein the allergen-containing material is a purified allergen preparation.

* * * * *